United States Patent [19]

Bédard

[11] Patent Number: 4,506,394
[45] Date of Patent: Mar. 26, 1985

[54] CARDIAC VALVE PROSTHESIS HOLDER

[75] Inventor: Pierre Bédard, Nepean, Canada

[73] Assignee: Molrose Management, Ltd., Ontario, Canada

[21] Appl. No.: 457,514

[22] Filed: Jan. 13, 1983

[51] Int. Cl.³ .............................................. A61F 1/22
[52] U.S. Cl. ..................................... 3/1.5; 128/334 R
[58] Field of Search ................... 3/1.5, 1; 128/334 R, 128/334 C

[56] References Cited

U.S. PATENT DOCUMENTS

| | | | |
|---|---|---|---|
| 3,503,079 | 3/1970 | Smith | 3/1.5 |
| 3,574,865 | 4/1971 | Hamaker | 3/1.5 |
| 3,996,623 | 12/1976 | Kaster | 3/1.5 |
| 3,997,923 | 12/1976 | Possis | 3/1.5 |

FOREIGN PATENT DOCUMENTS 1180087 10/1964 Fed. Rep. of Germany .......... 3/1.5

Primary Examiner—Ronald L. Frinks

[57] ABSTRACT

An implantable device which is suited for implantation into a human or animal heart for receiving and removably holding a valve prosthesis is described. The device comprises a ring structure which is adapted to be fixed to the tissue around the orifice of a heart valve after excision of the diseased or damaged natural valve has been effected. In use, the ring structure is fixed in place and then the appropriate valve prosthesis is attached to the ring. When the valve prosthesis fails and has to be replaced with a new prosthesis, the damaged prosthesis can be detached from the ring allowing a replacement prosthesis to be fixed to the ring without affecting the connection between ring structure and tissue.

6 Claims, 16 Drawing Figures

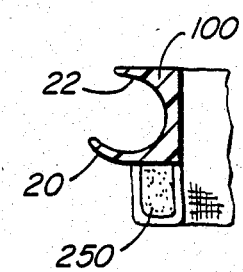 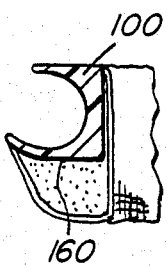 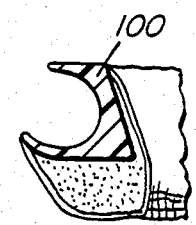
FIG. 10   FIG. 11   FIG. 12
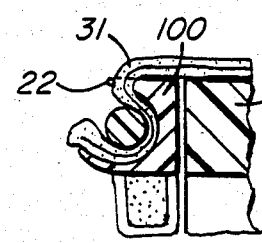 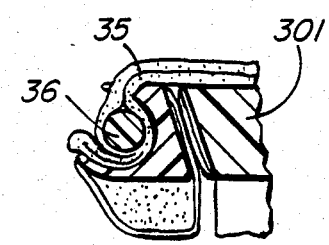
FIG. 13   FIG. 14
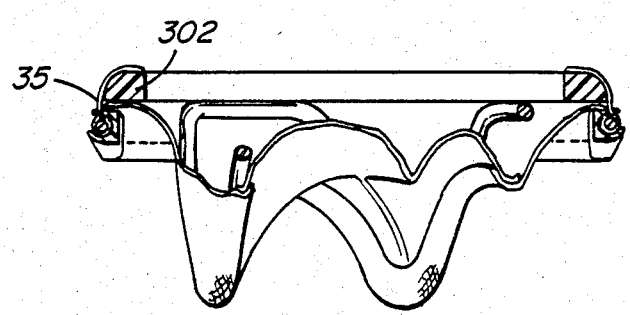
FIG. 15
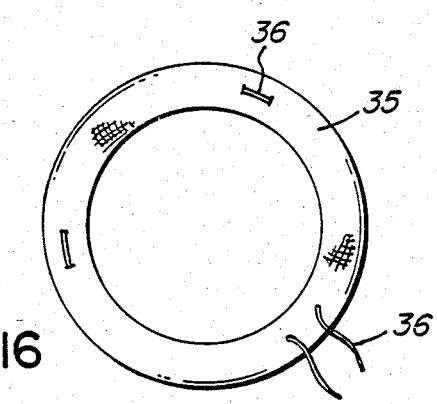
FIG. 16

CARDIAC VALVE PROSTHESIS HOLDER

This invention relates to a device adapted to be implanted into a human or animal heart for receiving and removably holding in place a valve prosthesis. More particularly, the invention relates to a ring arrangement adapted to be attached to tissue surrounding a diseased or damaged cardiac valve to facilitate insertion and replacement of a valve prosthesis.

An implantable device of this kind should be durable and last for many years while exposed to body fluids and wear caused by movement of the valve prosthesis relative to the ring in response to the constantly changing pressure exerted on the valve. Furthermore, such a ring arrangement requires provisions permitting the ring to be securely fixed to the tissue surrounding the valve orifice. In use, the ring should allow free flow through the valve and any obstruction of the valve orifice should be kept to a minimum such as by using a ring arrangement with an orifice substantially identical to that of the valve and the valve prosthesis. A ring of this kind further requires provisions for securing a valve prosthesis to the ring in such a way that the prosthesis can easily be replaced as required, but does not become disconnected unless removed by a surgeon. Moreover, the ring arrangement should be made of or covered with materials which are inert and also substantially non-thrombogenic.

Valve prostheses have been used to replace various diseased or damaged natural valves. Among the four heart valves, the aortic valve, the mitral valve, the pulmonic valve and the tricuspid valve, the aortic and mitral valves are most frequently replaced.

The mitral valve controls the flow of blood between the left atrium and the left ventricle and the aortic valve controls the blood flow from the left ventricle into the aorta.

Generally the known cardiac valve prostheses are either bioprostheses and mechanical prostheses. The bioprostheses are generally made of a suitable animal tissue on a metal or plastic frame while the mechanical prostheses are made entirely of metal and/or plastic material.

The valve prostheses are adapted to be stitched to the tissue surrounding the diseased valve that is being replaced. To this effect the valve prosthesis frame includes a generally circular structure, the valve seat, which is mostly made of metal or plastic and which is usually provided with a woven or knitted fabric to facilitate suturing. The fabric surrounding the circular structure and often also other parts of the valve frame is mostly called a sewing ring or skirt.

Heart valve prostheses are subject to severe wear and often have to be replaced after a relatively short time. Other factors which necessitate replacement of an implanted valve prosthesis are the patient's adverse reaction to the implant, physical or chemical changes in the components of the valve, particularly those components which are of biological origin, or other material failure.

Every time replacement of an implanted prosthesis is effected, the sutures holding the prosthesis in place have to be removed and the new valve prosthesis has to be stitched to the same tissue area as the previous one. In this way the tissue surrounding the valve orifice becomes perforated and scarred and with each replacement operation it becomes progressively more difficult to secure the implant to the tissue.

In an effort to test and compare the performance of various valve prostheses in vivo Wexler et al (J. Cardiovasc. Surg. (Torino) 11,236–38, 1970) proposes the temporary implantation of an elastic sewing ring into the heart of a laboratory animal in which the various prostheses are to be tested. Wexler's elastic sewing ring is made of rubber bands covered with fabric and provided with four wires which are looped around the rubber bands and extend through the fabric to facilitate gripping of the sewing ring. The sewing ring is placed around a valve prosthesis and inserted into the valve opening. The sewing ring is stitched to the tissue and in this way holds in place the prosthesis to be tested. When the testing of the thus implanted valve prosthesis is completed, generally after about 1 hour, the sewing ring is expanded to release the first valve prosthesis and allow insertion of the second. In this way the rubber sewing ring allows rapid replacement of the valve prosthesis. Of course, Wexler's rubber sewing ring is designed only for very short term use in animal tests. The ring could not safely be implanted for any long term use, since the material is subject to fairly rapid deterioration and since, even prior to any noticeable deterioration, the rubber ring could easily be accidentally disconnected from the valve prosthesis as a result of the pressure differentials encountered in the heart. Moreover the protruding wires are likely to cause damage to the surrounding tissue.

Accordingly, the present invention provides an implantable device such as a ring arrangement which is suited for implantation into a human or animal heart for receiving a valve prosthesis. The ring is adapted to be fixed to the tissue around the orifice of the heart valve after excision of the diseased or damaged natural valve has been effected. Once the ring is fixed in place the appropriate valve prosthesis can be attached to the ring. When the valve prosthesis fails and has to be replaced with a new prosthesis, the damaged prosthesis is detached from the ring and the new replacement prosthesis is fixed to the ring. Since the connection between the ring and the tissue is not affected by this replacement of valve prostheses no additional perforation of the tissue takes place. This has the advantage that the operation is less traumatic for the patient and that the new valve prosthesis is as securely attached to the tissue as the old one was, even if over the years the valve prosthesis has to be replaced several times.

As the life expectancy of most bioprostheses is presently not yet known, surgeons often hesitate to use a bioprosthesis due to the uncertainty as to how often it will have to be replaced. Mechanical prostheses are often used instead, even though bioprostheses have some intrinsic advantages over the mechanical prostheses. For example, bioprostheses are generally less thrombogenic than mechanical prostheses which means that, while patients with mechanical valve prostheses have to be maintained on anticoagulants, patients with a bioprosthesis do not generally require long term anticoagulant therapy. As implantation of a ring according to the invention considerably facilitates replacement of valve prostheses, whether mechanical or bioprostheses, the ring allows surgeons to use bioprostheses more freely.

Use of the ring arrangement according to the invention also reduces the risk of perivalvular leaks developing, i.e. of blood passing between the tissue and the prosthesis when the valve is closed. The reason for this is that, once the ring is fixed to the tissue, the connection between ring and tissue can be checked and, if necessary, repaired before the valve prosthesis is inserted and attached to the ring.

The ring arrangement according to the invention may be used in connection with most types of cardiac valve prostheses, whether mechanical or bioprosthesis. Only minor changes to the prosthesis may be necessary to allow secure and easy attachment of the respective prosthesis to the ring. Such minor changes would not alter the basic concept of the prostheses. As long as the shape of the annular seat and sewing ring of a prosthesis is not significantly altered, the prosthesis can be attached to the inventive ring arrangement.

The ring arrangement may have any convenient shape which allows effective securement of the ring to the tissue and which allows the valve prosthesis to be conveniently and securely attached to the ring as well as removed from the ring.

The ring arrangement according to the invention is made of inert material such as certain metals and plastic materials and/or certain fabrics which do not react with body fluids to which the ring is exposed and are, in particular, as little thrombogenic as possible. To further reduce any slight thrombogenic effect the ring material may have, the area of the ring which, in use, is in contact with the blood stream may be covered with any kind of non-thrombogenic fabric. In most cases it is advantageous to use a ring which retains its shape such as a ring made of slightly resilient, but substantially rigid material. Such a ring is generally easier to handle than a soft ring and allows the back pressure exerted on the valve prosthesis, during diastole in the case of the aortic valve prosthesis, to bear not only on the stitches connecting the ring to the tissue but also on the larger area of tissue on which the ring is supported.

In order that the ring can be securely fixed to the tissue surrounding the valve orifice, one of the following provisions may be made:

(a) The ring may be partially or completely covered with a knit or other fabric which facilitates suturing of the ring to the tissue, either with continuous or interrupted stitches.

(b) The ring may be provided around its periphery with eyelets which facilitate attachment of the ring with sutures.

(c) The ring may be provided with openings extending substantially in axial direction through the ring allowing suturing thread to be passed through.

(d) The ring may be provided at its periphery with a plurality of hook-like clamping extensions which permit clamping of the ring to the tissue.

When sutures are used to fix the ring arrangement to the tissue, it is important that the sutures are protected from wear due to the slight movement of the valve prosthesis relative to the ring. In cases when sutures are being passed through openings in the ring, it is desirable that the ring be provided with grooves for the thread, particularly on the surface(s) of the ring which, in use, are in contact with the valve prosthesis.

With regard to the connection between the ring arrangement according to the invention and the valve prosthesis it is important that, on the one hand, the valve prosthesis is attached to the ring sufficiently securely that accidental disconnection of the prosthesis is substantially prevented, while, on the other hand, the valve prosthesis can, when necessary, be detached from the ring relatively easily without affecting the attachment of the ring to the tissue.

The valve prosthesis may be connected to the ring in various ways, in most cases, however, the skirt of the valve prosthesis is used to attach the prosthesis to the ring. To this effect the skirt is advantageously made of slightly stretchable material and sufficiently long that it can be pulled over at least part of the outer periphery of the ring. In order to securely fasten the valve prosthesis to the ring one of the following provisions may be made:

(a) The ring may be provided at its periphery with a groove large enough to accommodate the skirt of the prosthesis and an appropriate size suturing thread. The latter is passed over the skirt around the periphery of the ring and tightened against the ring. Alternatively, the skirt of the prosthesis may already be provided with a thread so that the skirt merely has to be pulled over the ring until the thread can be tightened in the groove.

(b) The periphery of the ring may be provided with a number of hooks so that, when the skirt is pulled over the ring, the hooks engage the skirt. Generally the skirt is additionally tied below the hooks. The tying thread may be held in place by the hooks only or additionally by a groove. Either way the prosthesis can be securely attached and detached in a relatively short time.

(c) The periphery of the ring may be provided with eyelets, fabric or other means which allow stitching of the valve prosthesis to the ring in such a way that the stitches can be removed without affecting the sutures connecting the ring with the tissue.

(d) In addition to any of the aforementioned provisions the surface of the ring which, in use, contacts the valve prosthesis may have a radial groove which cooperates with a radial rib on the valve seat to reduce movement of the valve prosthesis relative to the ring.

The connections between valve prosthesis and ring may also be effected in several other ways.

(e) The ring and valve seat of the prosthesis may be provided with an appropriate groove and rib to effect a snap-in connection. Such a connection requires that either ring or valve seat are made of a sufficiently resilient material.

(f) The ring and valve seat may be provided with complementary screw threads. The prosthesis may be screwed either to the top of the ring, such as by provision of a threaded radial groove in the ring, or into the orifice of the ring. In the latter case the diameter of the orifice of the ring and at the same time the valve orifice is reduced and for this reason such a connection is only suitable for replacement of valves which have a relatively large orifice.

(g) The ring and valve seat may be provided with complementary hooks and retainers which engage when twisted relative to each other by a fraction of a turn.

(h) In cases when hook-like clamping extensions are attached to the periphery of the seat of the valve prosthesis the ring may be provided with fabric which permits clamping of the prosthesis to the ring, or, alternatively, the ring may be made of fabric, fabric pad or the like.

(i) The valve seat can be provided with suitable screw holes which correspond to screw holes in the ring. Thus, suitable screws can be put through the two sets of screw holes to attach the valve seat to the ring firmly. The screws preferably cannot be removed completely from the holes of the valve seat so that they will not become separated from the apparatus.

For best results the skirt of the valve prosthesis may be pulled over connections (e) to (g) and (i) and stitched or tied to the ring. This additonal measure helps to prevent accidental disconnection between prosthesis and ring. It also generally avoids possible growth of tissue into the dead spaces in such connections and thereby minimizes difficulties in disconnecting the prosthesis from the ring after several years.

To further ensure that the connection between ring and tissue is not accidentally severed at the time when the valve prosthesis is removed from the ring, a flange or the like may be connected to the periphery of the ring. The flange is intended to prevent the scalpel from penetrating along the periphery of the ring to the sutures holding the ring in place at the time when the thread and skirt are cut to remove the prosthesis.

The present invention will now be described in more detail by way of example only and with reference to the accompanying drawings.

FIG. 1 is a partial cross section of one embodiment of the invention;

FIG. 2 is a partial cross section of a second embodiment of the invention;

FIG. 3 is a top plan view of the embodiment of FIG. 1;

FIG. 4 is a partial cross section of a third embodiment of the invention;

FIG. 5 is a partial cross section of a fourth embodiment of the invention;

FIG. 6 illustrates in partial cross section the connection between the valve seat of an aortic valve prosthesis and the embodiment of FIG. 1;

FIG. 7 illustrates in partial cross section the connection between the valve seat of a second aortic valve prosthesis and the embodiment of FIG. 2;

FIG. 8 illustrates in partial cross section the connection between the valve seat of a third aortic valve prosthesis and a fifth embodiment of the invention;

FIG. 9 shows a schematic cross section of an aortic valve prosthesis connected to the embodiment of FIG. 1;

FIGS. 10 to 15 illustrate embodiments of the invention adapted to receive a mitral valve prosthesis;

FIG. 10 illustrates a partial cross section of a sixth embodiment of the invention;

FIG. 11 illustrates a partial cross section of a seventh embodiment of the invention;

FIG. 12 illustrates a partial cross section of a eighth embodiment of the invention;

FIG. 13 illustrates in partial cross section the connection between the valve seat of a mitral valve prosthesis and the embodiment of FIG. 10;

FIG. 14 illustrates in partial cross section the connection between a second mitral valve prosthesis and the embodiment of FIG. 12;

FIG. 15 shows a schematic cross section of a mitral valve prosthesis connected to the embodiment of FIG. 11; and FIG. 16 is a bottom view of the skirt of a valve prosthesis shown in FIGS. 7 and 15.

FIGS. 1 to 9 illustrate ring arrangements adapted to receive an aortic valve prosthesis. Ring 10 has a flat upper surface 12 on which the annular seat of the aorta valve prosthesis can be placed. The surface is equal to or slightly wider than the valve seat and may be about 2 mm wide. The inner surface 14 of the ring is smooth so that, when implanted, the ring forms a continuation of the annular valve seat and causes a minimum in disturbance in the blood flow.

A flange 20 is integrally connected with the ring on its outer surface. The flange may extend slightly upwardly as in FIGS. 1, 2 and 4 or may extend in radial outward direction as in FIG. 5.

Figure 1:
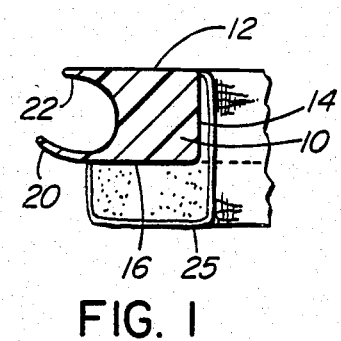
FIGS. 1 to 9 illustrate embodiments of the invention adapted to receive an aortic valve prosthesis.
Figure 4:
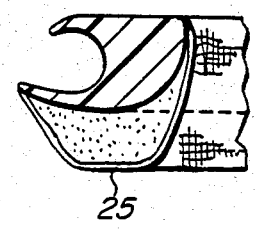
Figure 2:
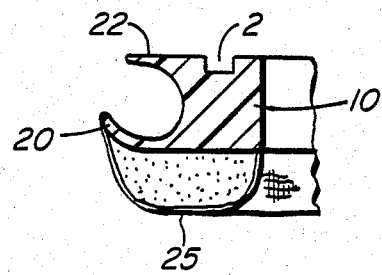
Figure 5:
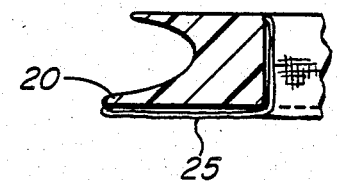
Figure 3:
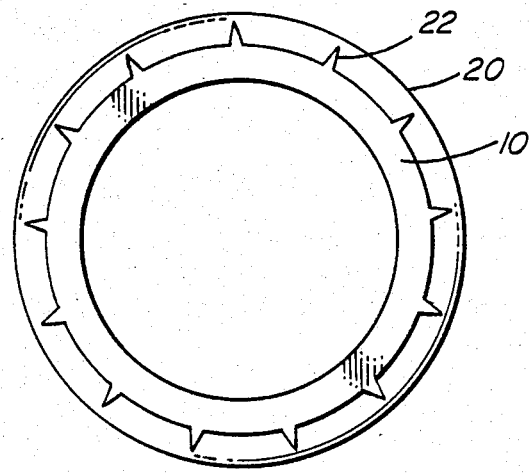

The radially outer surface of the ring 10 is further provided with a plurality of hooks 22 which are evenly spaced around the upper periphery of the ring and which in the illustrated embodiments are integral with the ring. The distance between the hooks shown in FIG. 3 is about 5 mm, but the hooks may also be arranged closer together or spaced further apart. The hooks can extend in radially outward direction as in FIGS. 1, 2 and 5 or be bent downward towards flange 20 as in FIG. 4. Either way the flange extends beyond the hooks in radial direction.

The rings illustrated in FIGS. 1 to 4 are each provided with a knit fabric 25 which in the illustrated embodiments is either arranged to cover inner surface 14 and lower surface 16 or substantially only lower surface 16. The fabric or portion of the fabric which extends over lower surface 16 may be padded as in FIGS. 1, 2 and 4 and it may extend over the ring only or over the ring and the flange. Upper surface 12 of the ring may also be covered with fabric.

Figure 6:
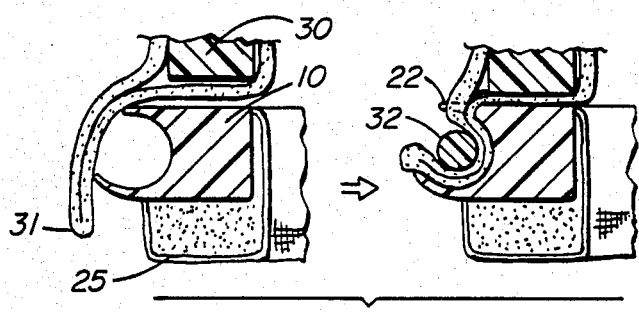
Figure 7:
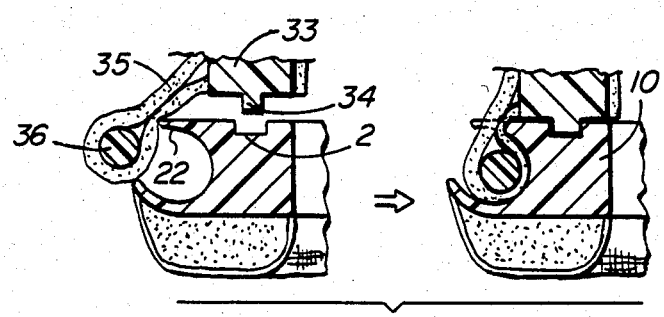
Figure 8:
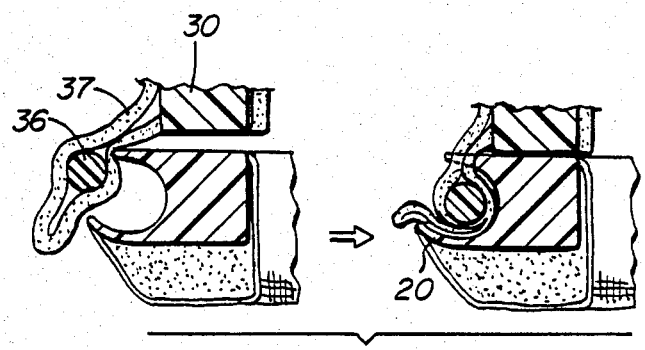

FIG. 6 illustrates the securement of a valve seat 30 of an aortic valve prosthesis on a ring arrangement according to the invention. Skirt 31 of the prosthesis is pulled down over hooks 22 of ring 10 and tied to the ring with a suturing thread 32. Valve seat 33 shown in FIG. 7 is provided with a rib 34 which cooperates with groove 2 in ring 10. Skirt 35 of the prosthesis shown in FIG. 7 is provided at its lower end with a suturing thread 36 to facilitate tying of the skirt around the ring. Skirt 37 of the prosthesis shown in FIG. 8 is also provided with a suturing thread 36, but the skirt 37 is longer and extends beyond the thread so that a loose portion of the skirt substantially covers the upwardly facing side of flange 20.

Figure 9:
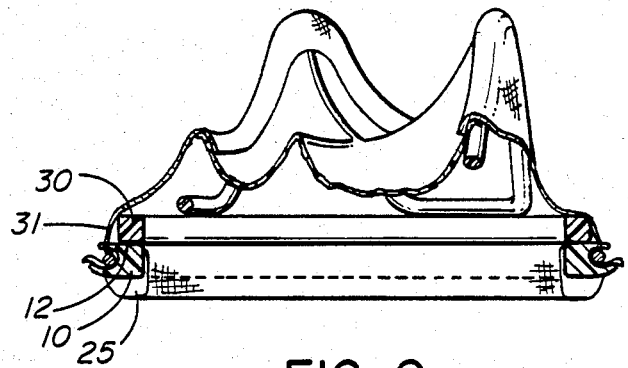

The illustrated ring arrangements are implanted into the aorta in such a way that the valve seat of an aortic valve prosthesis is positioned on the upper surface 12 of the respective ring and is attached to the ring as shown schematically in FIG. 9.

FIGS. 10 to 15 illustrate ring arrangements adapted to receive a mitral or tricuspid valve prosthesis. Ring 100 is similar to ring 10 in FIGS. 1 to 9 except that it is not as wide in radial direction. The embodiments shown in FIGS. 10 to 12 are each provided with a flange 20, a plurality of hooks 22 and a knit fabric cover 250. As in the case of the aortic valve the fabric or portion of fabric extending over the lower surface 160 of the ring may be padded and may extend over the ring only or over the ring and the flange. The upper surface of the ring may also be covered with fabric.

FIGS. 13 and 14 each illustrate possible connections between a valve seat of a mitral valve prosthesis to a ring according to the invention. Skirts 31 and 35 of the prostheses 300 and 301 are pulled over a respective ring 100 and over hooks 22 and tied to the ring. The illustrated ring arrangements for mitral valve prostheses are implanted into the left atrium in such a way that the prosthesis is positioned in the orifice of the ring and may be attached to the ring as shown in FIG. 15.

FIG. 16 illustrates the skirt of a valve prosthesis 302 when the skirt is modified to include a suturing thread as indicated in FIGS. 7 and 15. The thread 36 passes through the skirt with the ends of the thread hanging loosely from the skirt. To facilitate tightening of the skirt the thread is passed to the outside of the skirt in two places.

The surface portions of the valve prostheses which, in use, are in close contact with the respective ring arrangement may be covered with fabric or the like as illustrated in FIGS. 6, 14 and 15 or may not be covered as shown in FIGS. 7, 8, 9 and 13.

When a heart valve of a patient is diseased and has to be replaced the valve is removed in the known manner. The size of the valve orifice and the most suitable location for implanting of the prosthesis is assessed by insertion of a suitable obturator. The appropriate size and type of valve prosthesis and ring arrangement according to the invention are selected. In deciding on the size of the ring arrangement and its location in the heart as well as in choosing the valve prosthesis, it has to be taken care that obstruction of the natural valve orifice is kept to a minimum in order to ensure maximum efficiency of the heart pumping action and to avoid causing any unnecessary turbulence in the blood flow.

In many cases one kind of ring arrangement can accommodate a number of different valve prostheses. In other cases specific prostheses require specific ring arrangements. Valve prostheses for use with the ring arrangements illustrated in FIGS. 1 to 16 have to be provided with skirts which can be pulled over the ring and hooks. Such skirts are preferably made of slightly stretchable material and are provided with a thread. To keep tissue growth to a minimum the skirt material may be coated with silicon, Silastic (Trademark), Teflon (Trademark), or the like. In the case of mitral and tricuspid valve prostheses for use with the ring arrangements shown in FIGS. 10 to 15, it is preferred that the portion of the prosthesis which, in use, is in close proximity to the ring is covered with fabric, pads or the like to minimize friction between this portion of the valve prosthesis and the ring. This is particularly important in the case of bioprostheses, since the pericardium tissue generally used in such prostheses may be damaged by constant friction due to slight movement of the prosthesis relative to the ring.

While the chosen prosthesis is prepared for implanting, the ring is inserted.

In the case of an aortic valve the ring is inserted into the aorta in proximity to the aortic annulus above the orifice connecting the aorta with the left ventricle and below the ostia of the coronary arteries. If the ring is provided with clamps on its lower outer periphery or its lower surface, the clamps are tightened to anchor the ring in the tissue.

If, as in the embodiments of FIGS. 1 to 9 the ring is provided with thin fabric or preferably with a fabric pad on its lower surface, this fabric comes to sit on the aortic annulus. The suturing thread is passed through the tissue next to the patient's aortic annulus and then returned through the fabric. If interrupted sutures are preferred the suture is tied, otherwise the stitching is continued. If needed, a double needle stitch can be used. In this case two needles and threads are passed under the ring through the fabric pad from the outside of the ring orifice and returned through the aortic tissue below the ring to the outside. An upwardly directed flange facilitates passing of the needle underneath the ring. The two thread ends are then tied. A fabric pad on the ring generally allows a tight connection between ring and tissue. If desired, pledgets may be used to reduce the possibility of cutting or tearing the tissue when tightening the suture. In this situation, the two needles and threads are first passed through the tissued next to the aortic annulus and then through the fabric pad of the ring arrangement. The two thread ends are tied right away or following placement of stitches around the annulus. A similar procedure may be applied, if the ring arrangement is provided with eyelets or openings to receive sutures.

After the sutures are completed the connection between ring and tissue is carefully checked in an effort to prevent development of perivalvular leaks or dehiscence once the prosthesis is in place.

The desired aortic valve prosthesis can now be inserted. To this effect the skirt or sewing ring of the valve prosthesis is turned upwardly from the annular valve seat and the valve seat is placed on the ring. For the aortic valve it is preferred that the prosthesis is placed on the ring in such a way that the orifice of the valve prosthesis coincides with the ring orifice.

In the illustrated embodiments the skirt of the prosthesis is then rolled down over the hooks and, if the skirt is not already provided with a thread, a suturing thread is passed around the ring and tied so that the skirt is tightly pressed against the ring. The hooks substantially prevent the skirt from pulling out of the thread and the thread from slipping off the ring. The flange prevents the thread from moving downwardly. In this way the prosthesis is securely fastened to the ring and can withstand the varying pressures in the aorta. Optionally, the hooks may be coated with a non-toxic substance, such as a fluorescent substance, which enhances visibility of the hooks.

In cases where snap-in, screw, hook and retainer and similar connections are used, these connections are effected before the skirt is rolled down, if the use of an extended skirt is desired.

In the case of a mitral or tricuspid valve the ring is inserted into the left atrium close to the orific connecting the left atrium with the left ventricle and the ring is connected to the mitral annulus in practically the same way as in the case of the aortic valve. After checking the connection between ring and tissue the desired mitral valve prosthesis is inserted into the ring orifice so that it extends into the natural valve opening. Depending on the prosthesis the valve seat may be positioned on the ring or in the ring orifice. In the illustrated embodiments of FIGS. 10 to 15 the skirt of the prosthesis is pulled over the ring and hooks and is tied as described above. It has to be taken care that the skirt is anchored to the hook and tied securely, since in the mitral and tricuspid valves the forces exerted on the closed valve prosthesis in systole bear on the skirt and not mainly on the ring as in the case of the aortic valve. For the same reason a mitral or tricuspid valve prosthesis of this kind should be provided with a strong skirt material.

If screw connections or the like are used, these are effected with or without use of the skirt as indicated above.

In order to reduce any thrombogenic effect the ring material may have, it is preferred that the surfaces of the ring which come into contact with blood and which are not already covered with fabric, are covered by the skirt of the prosthesis.

When a valve prosthesis which is connected to a ring arrangement according to the invention fails due to wear or any other reason, the valve prosthesis is removed from the ring.

In valve prostheses which are connected to the ring as illustrated in FIGS. 6 to 9 or 13 to 15 the skirt of the prosthesis is first severed around the valve seat so that the valve prosthesis can be removed. Following this the thread holding the skirt to the ring is cut and removed together with the rest of the skirt.

As this thread is generally in proximity to the sutures which hold the ring in place, there is the danger of accidentally cutting one of these sutures. Flanges of the kind illustrated facilitate cutting of the thread without inadvertently damaging the connection between ring and tissue.

If screw or other connections are used, these are disconnected after the skirt, if any, has been severed, thus allowing the valve to be removed.

A new valve prosthesis can then be inserted and connected to the ring arrangement in any of the aforementioned ways.

I claim:

1. An implantable device for receiving and removably holding in place a cardiac valve prosthesis comprising a substantially ring-shaped structure provided with means allowing the strucutre to be securely attached to heart tissue and with a plurality of hooks connected to the generally radially outwardly facing portion of the structure and adapted for receiving and retaining a sewing skirt of a valve prosthesis for removably connecting a valve prosthesis to said structure, and a flange connected to the radially outwardly facing portion of the structure and extending substantially radially outwardly.

2. An implantable device for receiving and removably holding in place a cardiac valve prosthesis comprising a substantially ring-shaped structure, fabric covering a portion of said structure, said fabric allowing the structure to be securely sutured to heart tissue, a plurality of hooks connected through the generally radially outwardly facing portion of the structure and adapted for receiving and retaining a sewing skirt of a valve prosthesis, and a flange extending substantially radially outwardly from the structure.

3. An implantable device for receiving and removably holding in place in a human or animal heart a cardiac valve prosthesis comprising a substantially ring-shaped structure; fabric covering a portion of said structure, said fabric allowing the structure to be sutured to heart tissue so as to, in use, substantially avoid blood leaks; a plurality of hooks integrally connected to the generally radially outwardly facing portion of the structure, distributed substantially evenly around the circumference of the structure, and adapted for receiving and retaining a sewing skirt of a valve prosthesis; and a flange extending substantially radially outwardly from the structure and separating the portion of the structure to which the hooks are connected from the portion which is covered with fabric such that, in use when a valve prosthesis, the skirt of which is retained by said hooks and by tying, is replaced, the skirt of the valve prosthesis can be removed from the structure without affecting the connection between the structure and heart tissue.

4. An implantable device for receiving and removably holding in place an aortic valve prosthesis comprising a generally rigid substantially ring-shaped structure provided with a padded fabric covering the portion of said structure which is adapted to sit on aortic tissue to allow the structure to be securely sutured to aortic tissue and with a plurality of hooks connected to the generally radially outwardly facing portion of the structure and adapted for receiving and retaining a sewing skirt of a valve prosthesis and for holding in place a suturing thread for tying the sewing skirt to the structure for removably connecting an aortic valve prosthesis to said structure such that the aortic valve prosthesis is positioned on the structure and the orifice of the valve prosthesis substantially coincides with the orifice of the ring.

5. An implantable device for receiving and removably holding in place a cardiac valve prosthesis comprising a substantially ring-shaped structure provided with a padded fabric covering the portion of said structure which is adapted to be sutured to heart tissue to allow the structure to be securely sutured to heart tissue and with a plurality of hooks connected to the generally radially outwardly facing portion of the structure and adapted for receiving and retaining a sewing skirt of a valve prosthesis and for holding in place a suturing thread for tying the sewing skirt to the structure for removably connecting a mitral or tricuspid valve prosthesis to said structure such that the valve prosthesis is positioned in the orifice of the structure.

6. A device as in claim 4 or 5 further comprising a flange separating the portion of the structure to which the hooks are connected from the portion to which the padded fabric is attached such that, in use when a valve prosthesis, the skirt of which is retained by said hooks and by tying, is replaced, the skirt of the valve prosthesis can be removed from the structure without affecting the connection between the structure and heart tissue.

* * * * *